United States Patent
Dawson

(10) Patent No.: US 7,350,522 B2
(45) Date of Patent: *Apr. 1, 2008

(54) SCANNING METHOD FOR APPLYING ULTRASONIC ACOUSTIC DATA TO THE HUMAN NEURAL CORTEX

(75) Inventor: Thomas Patrick Dawson, Escondido, CA (US)

(73) Assignees: Sony Corporation, Tokyo (JP); Sony Electronics, Park Ridge, NJ (US)

( * ) Notice: Subject to any disclaimer, the term of this patent is extended or adjusted under 35 U.S.C. 154(b) by 310 days.

This patent is subject to a terminal disclaimer.

(21) Appl. No.: 10/823,090

(22) Filed: Apr. 12, 2004

(65) Prior Publication Data

US 2004/0267118 A1 Dec. 30, 2004

Related U.S. Application Data

(60) Continuation-in-part of application No. 10/353,225, filed on Jan. 28, 2003, now Pat. No. 6,729,337, which is a division of application No. 09/690,571, filed on Oct. 17, 2000, now Pat. No. 6,536,440.

(51) Int. Cl.
*A61B 19/00* (2006.01)
(52) U.S. Cl. .................. 128/897; 128/898; 601/2
(58) Field of Classification Search ......... 600/300, 600/438–439; 601/2–4; 128/897–898; 623/4.1, 623/10, 24, 66.1, 902
See application file for complete search history.

(56) References Cited

U.S. PATENT DOCUMENTS 3,848,608 A 11/1974 Leonard ............. 128/419 R 4,343,301 A 8/1982 Indech ..................... 128/24

(Continued)

OTHER PUBLICATIONS

Ensminger, Dale. Ultrasonics Fundamentals, Technology Applications. Columbus, Ohio. pp. 373-376.

(Continued)

*Primary Examiner*—Francis J. Jaworski
(74) *Attorney, Agent, or Firm*—Mayer & Williams PC; Karin L. Williams, Esq.

(57) ABSTRACT

A method for creating sensory experiences operates by scanning the acoustical signal across the human neural cortex to create the desired sensory perceptions. The acoustic signal is scanned in a predetermined pattern. The pattern is then modified to fill in spaces in the predetermined pattern so that over a short time period, the desired signal is scanned across the intended region of the neural cortex. In one exemplary embodiment, the pattern begins with an array of points on the cortex. Thus, an acoustic signal in an array of points is directed towards the cortex. The acoustic pattern is then shaped to expand in radius about each point. Thus, the acoustic signal scans the visual cortex in an array of expanding circles. Varying the signal at each point along the radius as it expands produces neural firing differences in the neural tissue. When the circles expand to where they begin to touch, the pattern changes to fill in the areas between the original array of points. The new circles are centered about the points between the original stimulation locations, and the acoustic signal contracts about these new centers. The signal continues to contract about the new center points. When the new circles have contracted to an array of points, the process can be repeated from the start or simply reversed. Another method operates by forming concentric circles and expanding and contracting each of the concentric circles to fill in the original spaces between the concentric circles.

17 Claims, 12 Drawing Sheets

U.S. PATENT DOCUMENTS

| | | | | |
|---|---|---|---|---|
| 4,611,596 | A | 9/1986 | Wasserman | 128/419 R |
| 4,628,933 | A | 12/1986 | Michelson | 128/419 R |
| 4,664,117 | A | 5/1987 | Beck | 128/897 |
| 4,883,067 | A | 11/1989 | Knispel | 128/732 |
| 4,979,508 | A | 12/1990 | Beck | 128/419 R |
| 5,031,154 | A | 7/1991 | Watanabe | 367/8 |
| 5,097,326 | A | 3/1992 | Meijer | 358/94 |
| 5,109,844 | A | 5/1992 | DeJuan, Jr. et al. | 128/419 R |
| 5,159,927 | A | 11/1992 | Schmid | 128/419 R |
| 5,179,455 | A | 1/1993 | Garlick | 359/9 |
| 5,651,365 | A | 7/1997 | Hanafy et al. | 128/622.03 |
| 5,738,625 | A | 4/1998 | Gluck | 128/897 |
| 5,853,370 | A | 12/1998 | Chance | 600/473 |
| 5,935,155 | A | 8/1999 | Humayun et al. | 607/54 |
| 5,956,292 | A | 9/1999 | Bernstein | 367/140 |
| 5,971,925 | A | 10/1999 | Hossack et al. | 600/443 |
| 6,017,302 | A | 1/2000 | Loos | 600/28 |
| 6,394,969 | B1 * | 5/2002 | Lenhardt | 601/2 |
| 6,511,429 | B1 * | 1/2003 | Fatemi et al. | 600/443 |
| 6,709,407 | B2 * | 3/2004 | Fatemi | 600/559 |
| 6,889,085 | B2 * | 5/2005 | Dawson | 607/54 |

OTHER PUBLICATIONS

Gavrilov, L. R.; Gershuni, G. V.; Pudov, V. I.; Rozenblyum, A. S.; Tsirulnikov, E. M. "Human hearing in connection with the action of ultrasound in the megahertz range on the aural labyrinth". American Institute of Physics. pp. 290-292.

Schwartz, Eric L.; Merker, Bjorn; Wolfson, Estarose; Shaw, Alan. "Applications of Computer Graphics and Image Processing to 2D and 3D Modeling of the Functional Architecture of Visual Cortez". Computational Neuroscience 13.

Normann, Richard A. Http://www.bionictech.com. Center for Neural Interfaces.

Whithouse, David Sci/Tech Computer uses cat's brain to see.

The Whitaker Center for Medical Ultrasonic Transducer Engineering. PennState College of Engineering. kksbio@engr.psu.edu.

Dpmi.tu-graz.ac.at/research/BCI; Brain Computer Interface.

Ipaustralia.gov.au/fun/patents/02_ear.htm. Bionic Ear Patent. Melbourne University, Australian Patent 519851. filing date 1978.

Williams, Earl G. "Measurement and Projection of Acoustic Fields". Nava Research Laboratory, Code 5137, Washington DC 20375.

Wall, Judy. "Resonance". Newsletter of the Bioelectromagnetics Special Interest Group. pp. 11-13, 15-16.

Mihran, Richard T.; Barnes, Frank S.; Wachtel, Howard. "Transient Modification of Nerve Excitability in Vitro By Single Ultrasound Pulses". Department of Electrical and Computer Engineering, University of Colorado. 1990.

Mihran, Richard T.; Barnes, Frank S.; Wachtel, Howard. "Temporally-specific modification of myelinated axon excitability in vitro following a single ultrasound pulse". Ultrasound Med Biol Department of Electrical and Computer Engineering, Univ. of Colorado. 1990. pp. 297-309.

Maynard, J.D.; Williams, E. G.; Lee, Y. Nearfiled acoustic holography:n I. Theory of generalized holography and the development of NAH, no date.

Stanley, Garrett B.; Le, Fei F.; Dan, Yang. "Reconstruction of Natural Scenes from Ensemble Responses in the Lateral Geniculate Nucleus". Depart. Of Molecular and Cell Biology, Div. of Neurobiology, Univ. of Calif. The Journal of Neuroscience. 1999. pp. 8036-8042.

Ensminger, Dale. Ultrasonics Fundamentals, Technology Applications. Columbus, Ohio. pp. 373-376, no date.

Gavrilov, L. R.; Gershuni, G. V.; Pudov, V. I.; Rozenblyum, A. S.; Tsirulnikov, E. M. "Human hearing in connection with the action of ultrasound in the megahertz range on the aural labyrinth". American Institute of Physics. pp. 290-292, undated.

Norman, Richard A.; Maynard, Edwin M.; Guillory, K. Shane; Warren, David J. "Cortical Implants for the Blind". Cortical Implants for the Blind. The Institute of Electrical and Electronics Engineers, Inc. 1996.

Schwartz, Eric L.; Merker, Bjorn; Wolfson, Estarose; Shaw, Alan. "Applications of Computer Graphics and Image Processing to 2D and 3D Modeling of the Functional Architecture of Visual Cortex". Computational Neuroscience 13, undated.

Lange, Larry. "Treading fine line between man and machine, researchers pursue silicon prostheses—Chip implants: weird science with a noble purpose—Second of two parts". CMPnet. The Technology Network. Feb. 10, 1997.

Matsumoto, Craig. "Papers outline biochips to restore eyesight, movement". EETIMESonline. www.cmpnet.com. The Technology Network. 1999.

"Encoding of Binocular Disparity by Complex Cells in the Cat's Visual Cortex". JN Online. The Journal of Neurophysiology. vol. 77. No. 6. 1997. pp. 2879-2909.

Normann, Richard A. Http://www.bionictech.com. Center for Neural Interfaces, no date.

Whithouse, David. Sci/Tech Computer uses cat's brain to see, no date.

The Whitaker Center for Medical Ultrasonic Transducer Engineering. PennState College of Engineering. kksbio@engr.psu.edu, no date.

Dpmi.tu-graz.ac.at/research/BCI; Brain Computer Interface, no date.

Ipaustralia.gov.au/fun/patents/$02_{13}$ ear.htm. Bionic Ear Patent. Melbourne University, Australian Patent 519851. filing date 1978.

Williams, Earl G. "Measurement and Projection of Acoustic Fields". Nava Research Laboratory, Code 5137, Washington DC 20375, no date.

Wall, Judy. "Resonance". Newsletter of the Bioelectromagnetics Special Interest Group. pp. 11-13, 15-16, no date.

* cited by examiner

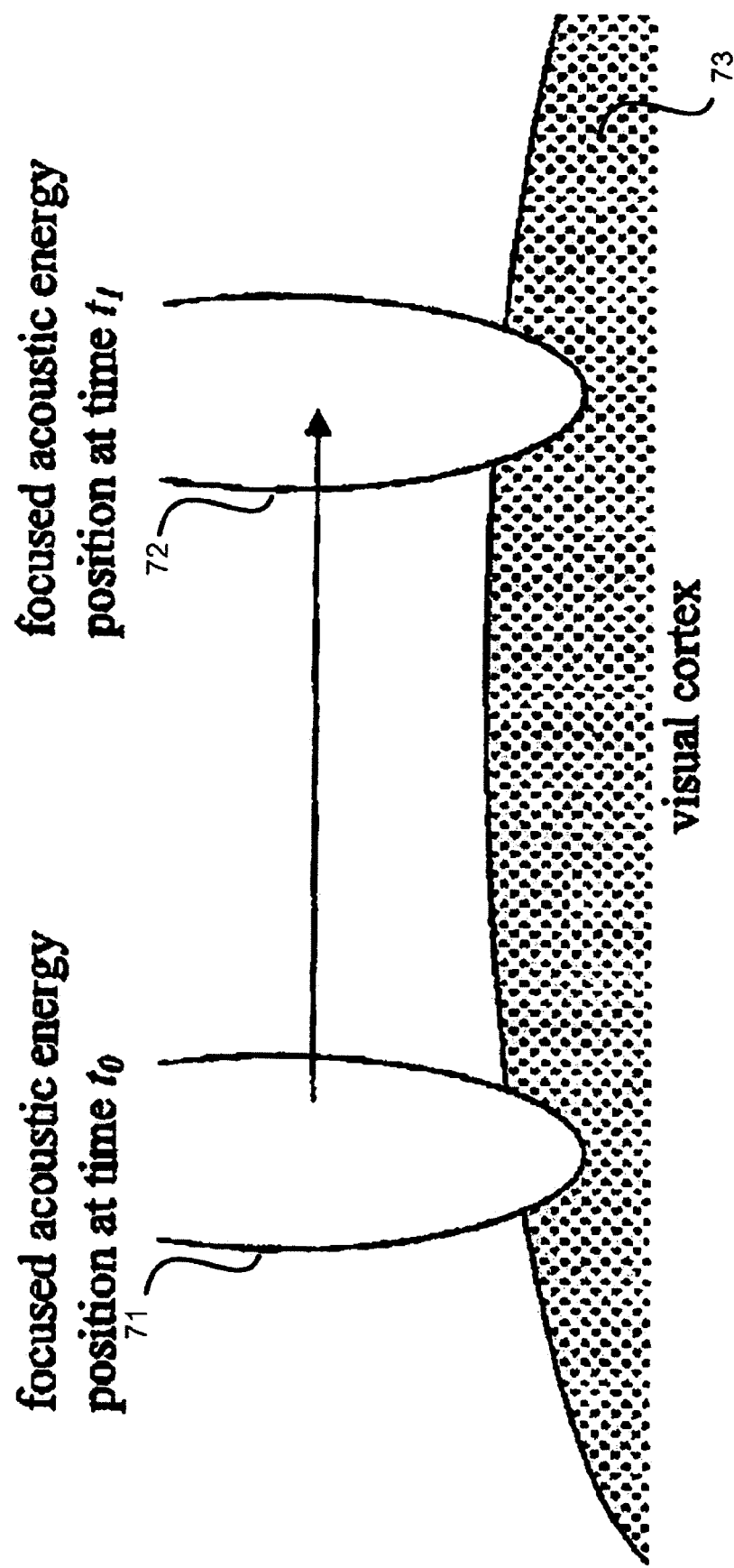

FIG 8

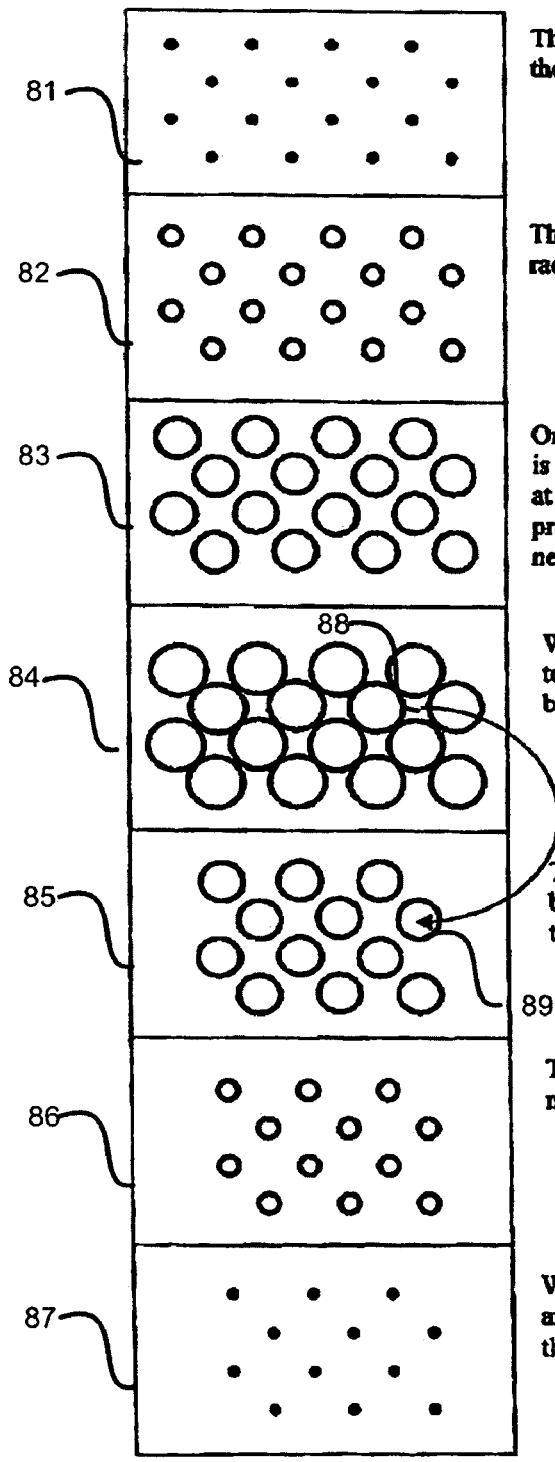

80

81 — The pattern begins with an array of points on the visual cortex.

82 — The acoustic pattern is shaped to expand in a radius about each point.

83 — Only the tissue along the edge of each radius is affected at any moment. Varying the signal at each point along the radius as it expands produces neural firing rate differences in the neural tissue.

84 — 88 When the radii expand to where they begin to touch the pattern changes to fill in the areas between the original point array.

85 — The new radii are centered about the points between the original stimulation locations and the signal contracts about these new centers.

89

86 — The signal continues to contract about the new center points.

87 — When the new radii have contracted to an array of points the process can repeated from the start or simply reversed.

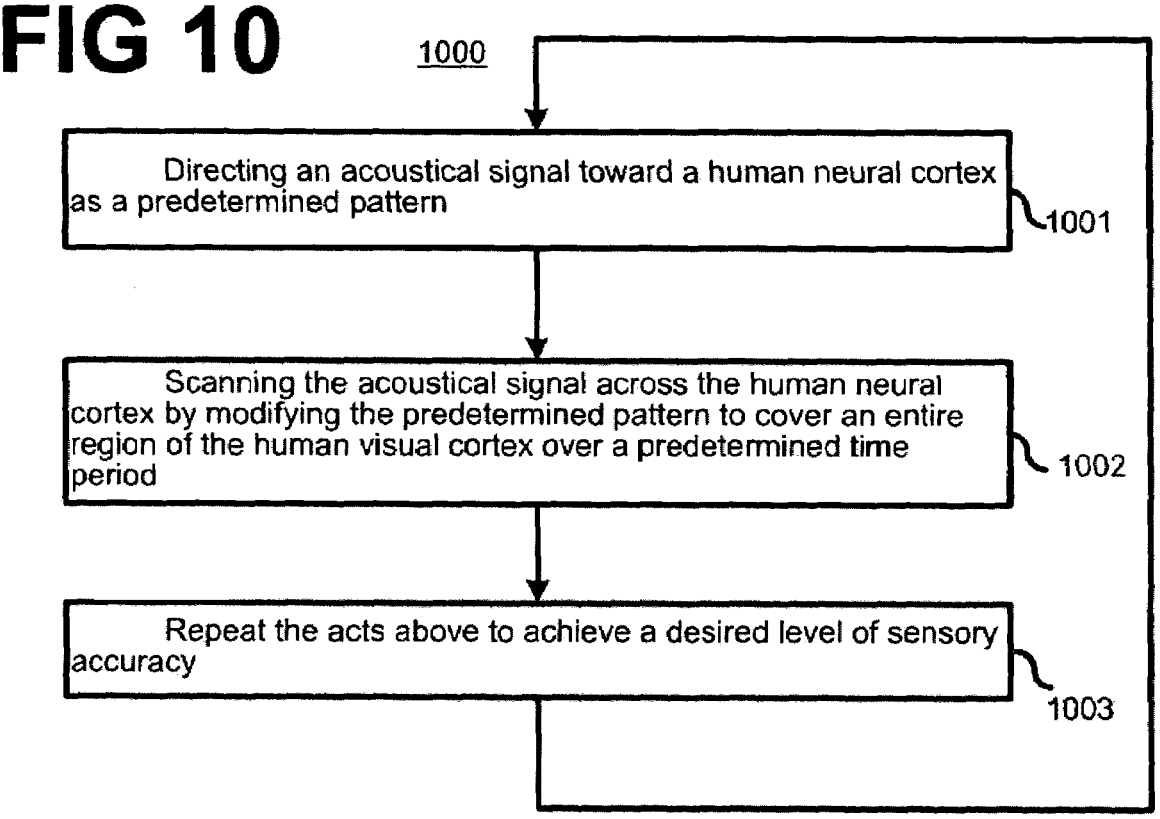

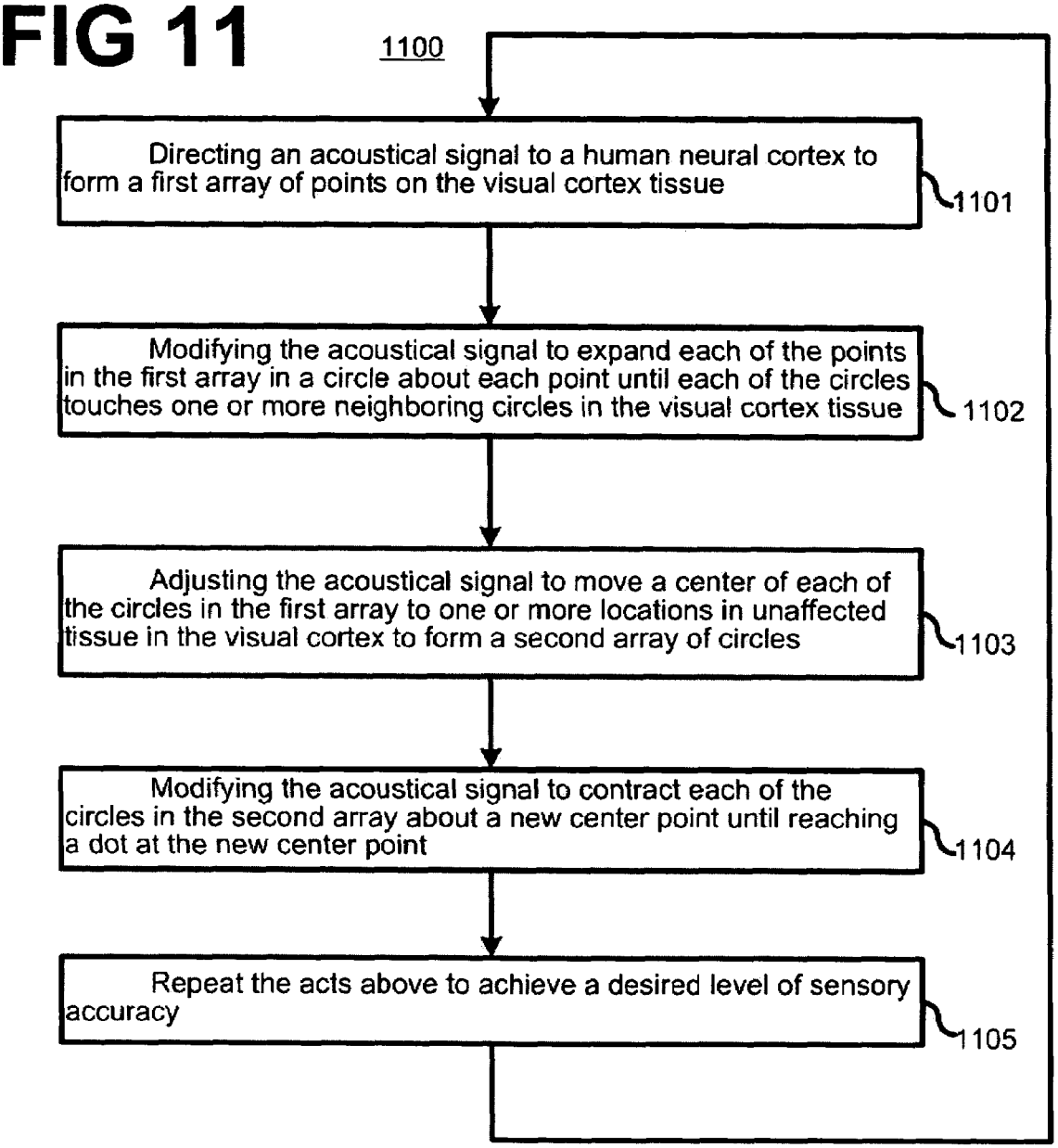

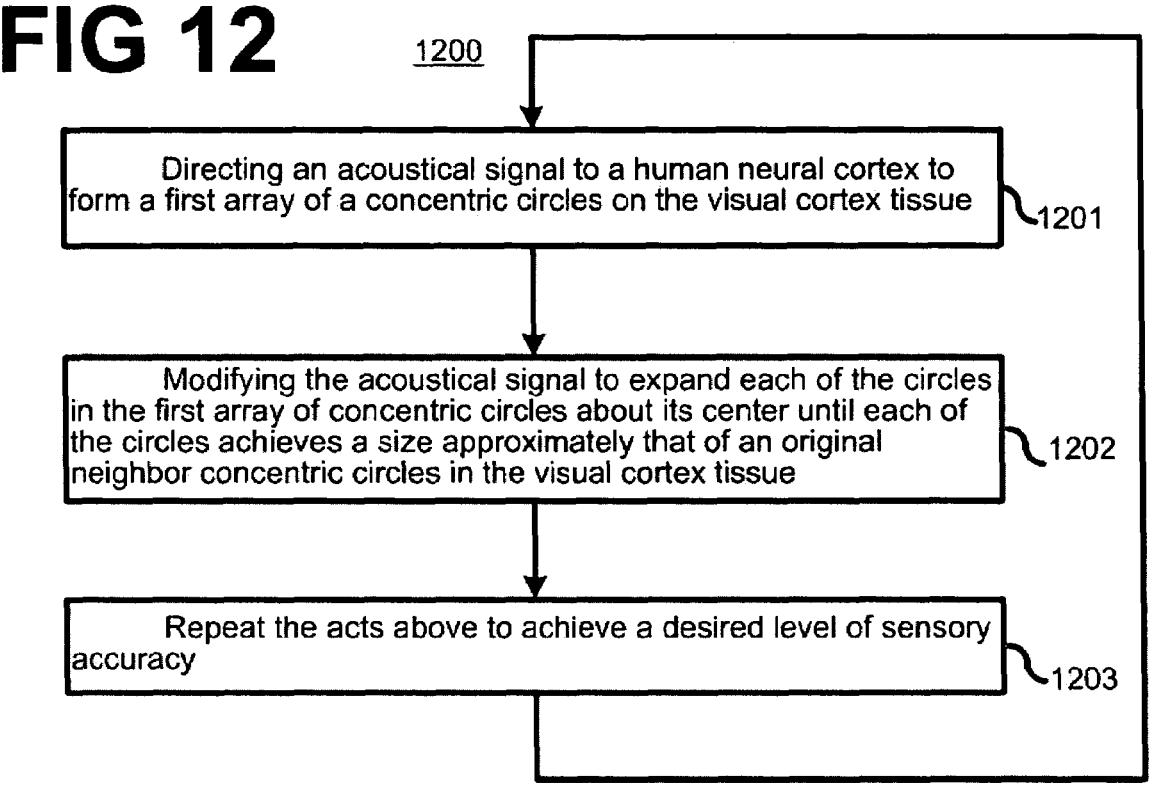

SCANNING METHOD FOR APPLYING ULTRASONIC ACOUSTIC DATA TO THE HUMAN NEURAL CORTEX

STATEMENT OF RELATED APPLICATIONS

This application is a continuation-in-part of U.S. patent application Ser. No. 10/353,225, filed Jan. 28, 2003, entitled "Method And System For Generating Sensory Data Onto The Human Cortex," now U.S. Pat. No. 6,729,337, which is a divisional of U.S. patent application Ser. No. 09/690,571, filed Oct. 17, 2000, also entitled "Method And System For Generating Sensory Data Onto The human Cortex," now U.S. Pat. No. 6,536,440. The specification of each of the above parent patent applications is incorporated by reference in its entirety herein.

FIELD OF THE INVENTION

The present invention relates generally to methods and systems for generating sensory experiences. More particularly, the present invention relates to a method and system for generating a sensory experience using an acoustic signal directed to a human neural cortex.

BACKGROUND conventional technique for generating neural activity in the human nervous system requires surgical implants. The implants may comprise electronic connections and wires that cause electronic impulses to interact with some portion of the human nervous system, such as the human neural cortex, and thereby cause neural activity in the human neural cortex. Researchers have successfully mapped audio sensory data to the cochlear channel, and visual data to the visual cortex.

Conventional invasive techniques have several drawbacks. First, surgical implants may cause patient trauma and medical complications during and/or after surgery. Second, additional or on-going surgery may be required, particularly if new technology is developed.

The present invention is therefore directed to a method for generating sensory experiences using a non-invasive technique.

SUMMARY OF THE INVENTION

The present invention solves the foregoing drawbacks by providing a non-invasive system and process for generating/projecting sensory data (visual, audio, taste, smell or touch) within/onto the human neural cortex. Moreover, the present invention provides a non-invasive system and process that uses acoustic signals to generate sensory data, e.g., visual, audio, taste, smell or touch, within/onto the human neural cortex. The system forms acoustic signals from externally supplied neural timing difference data. For example, imagery captured from a video camera is converted into neural timing difference data. An acoustic signal is then created to replicate these neural timing differences in the human cortex. Pulsed ultrasonic signals modify the firing rate of neural tissue. Controlled use of this pulsed data through ultrasonic holography allows neural timing differences to be placed into the cortex. Sensory experiences arise from differences in neural firing times.

One embodiment of the system comprises a primary transducer array and a secondary transducer array. The primary transducer array acts as a coherent or nearly coherent signal source. The secondary transducer array acts as a controllable, acoustical diffraction pattern that shapes, focuses and modulates energy from the primary transducer onto the neural cortex in a desired pattern. The secondary transducer emits acoustical energy that may be shifted in phase and amplitude relative to the primary array emissions. This arrangement provides the means to employ acoustic holography to apply the neural timing difference information to the cortex.

The pattern of energy is constructed such that each portion of the pattern projected into the neural cortex may be individually pulsed at low frequency. The system produces low frequency pulsing by controlling the phase differences between the emitted energy of the primary and secondary transducer array elements. The pulsed ultrasonic signal alters the neural firing timing in the cortex. Changes in the neural firing timing induce various sensory experiences depending on the location of the firing timing change in the cortex. The mapping of sensory areas of the cortex is known and used in current surgically invasive techniques. Thus, the system induces recognizable sensory experiences by applying ultrasonic energy pulsed at low frequency in one or more selected patterns on one or more selected locations of the cortex.

One of the advantages of the present system is that no invasive surgery is needed to assist a person, such as a blind person, to view live and/or recorded images or hear sounds.

One advantage of the system is its adaptability to each individual user. Human brains have some similarities, but they may vary in size, shape, number of convolutions, etc. The present system comprises components that may be calibrated and a library of acoustic signals that may be customized for each individual user. The system is advantageously configured to allow vision-impaired and/or hearing-impaired users to experience at least some visual and/or auditory sensations.

Another advantage of the system is that no invasive surgery is needed to assist a person, such as a blind or deaf person, to experience live or recorded images or sounds.

One embodiment of the system comprises a primary transducer array and a secondary transducer array. The primary transducer array acts as a coherent or nearly-coherent signal source. The secondary transducer array acts as a controllable, acoustic diffraction pattern that shapes, focuses and modulates energy from the primary transducer onto the neural cortex in a desired pattern. The secondary transducer emits acoustic energy that may be shifted in phase and amplitude relative to the primary array emissions.

The projected, ultrasonic sensory pattern of energy is configured such that each portion of the pattern projected into the neural cortex may be individually pulsed at low frequencies. The system produces low frequency pulsing by controlling the phase differences between the emitted energy of the primary and secondary transducer array elements. The ultrasonic signal pulsed at low frequencies affects the neural firing timing in the cortex. Even though a person may be blind or have his or her eyes closed, the person's visual cortex neurons are still firing. Changes in the neural firing timing induce various sensory experiences, depending on the altered firing time and the location of the neuron in the cortex. The mapping of some sensory areas of the cortex is known and used in current surgically invasive techniques. The present system induces recognizable sensory experiences by applying ultrasonic energy pulsed at low frequency in one or more selected patterns on one or more selected locations of the cortex.

One aspect of the invention relates to a method of storing data related to acoustic signals configured to alter neural firing times in a brain. The method comprises non-invasively projecting a first acoustic signal into the brain. The first acoustic signal affects a neural firing time at a first neural location in the brain. The method stores a user sensory response and data related to the first acoustic signal in a memory. The method non-invasively projects a second acoustic signal into the brain, and stores a user sensory response and data related to the second acoustic signal in the memory.

Another aspect of the invention relates to a method of customizing a library of data related to acoustic signals configured to alter neural firing times in a brain. The method comprises retrieving data related to a first acoustic signal from a memory; projecting a first acoustic signal into the brain using the data related to a first acoustic signal, the first acoustic signal affecting a neural firing time at a first neural location in the brain; storing a user sensory response with the data related to the first acoustic signal in the memory; retrieving data related to a second acoustic signal form the memory; projecting a second acoustic signal into the brain using the data related to the second acoustic signal; and storing a user sensory response with the data related to the second acoustic signal in the memory.

Another aspect of the invention relates to a system of storing data related to acoustic signals configured to alter neural firing times in a brain. The system comprises a transducer system configured to non-invasively project a first acoustic signal and a second acoustic signal into the brain, the first and second acoustic signal affecting one or more neural firing times at one or more neural locations in the brain; a signal generator coupled to the transducer system; and a memory coupled to the signal generator. The memory is configured to store: data related to the first and second acoustic signals; and user sensory responses produced by the first and second acoustic signals. The signal generator is configured to select data in the memory related to signals configured to generate the neural firing time differences in the brain, the transducer system is configured to apply the signals to generate the neural firing time differences in the brain.

These and other advantages of the present invention will become apparent to those skilled in the art upon a reading of the following specification of the invention and a study of the several figures of the drawing.

BRIEF DESCRIPTION OF THE DRAWINGS

FIG. 7 depicts a detailed view of two implantable electrodes in the array of FIG. 6 according to another aspect of the present invention.

FIG. 8 depicts an image being generated on a human neural cortex in various time stages using a method for activating the implantable electrode array of FIG. 6 according to yet another aspect of the present invention.

FIG. 10 depicts an exemplary embodiment of a method for generating sensory experiences according to yet another aspect of the present invention.

FIG. 11 depicts another exemplary embodiment of a method for generating sensory experiences according to still another aspect of the present invention.

FIG. 12 depicts yet another exemplary embodiment of a method for generating sensory experiences according to yet another aspect of the present invention.

DETAILED DESCRIPTION

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

U.S. Pat. Nos. 6,536,440 and 6,584,357 provide techniques for writing sensory data directly to the human neural cortex. These patents describe applying an acoustic signal to generate neural timing differences that result in perceived sensory experiences. Implanted arrays of electrodes produce a visual field of "dots" because the electrode locations are fixed and thus the neural timing difference is only between the tip of the electrode and the affected neural tissue (see FIG. 1).

A method to stimulate an entire area of neural tissue is required rather than the selected pinpoint locations.

Figure 1:
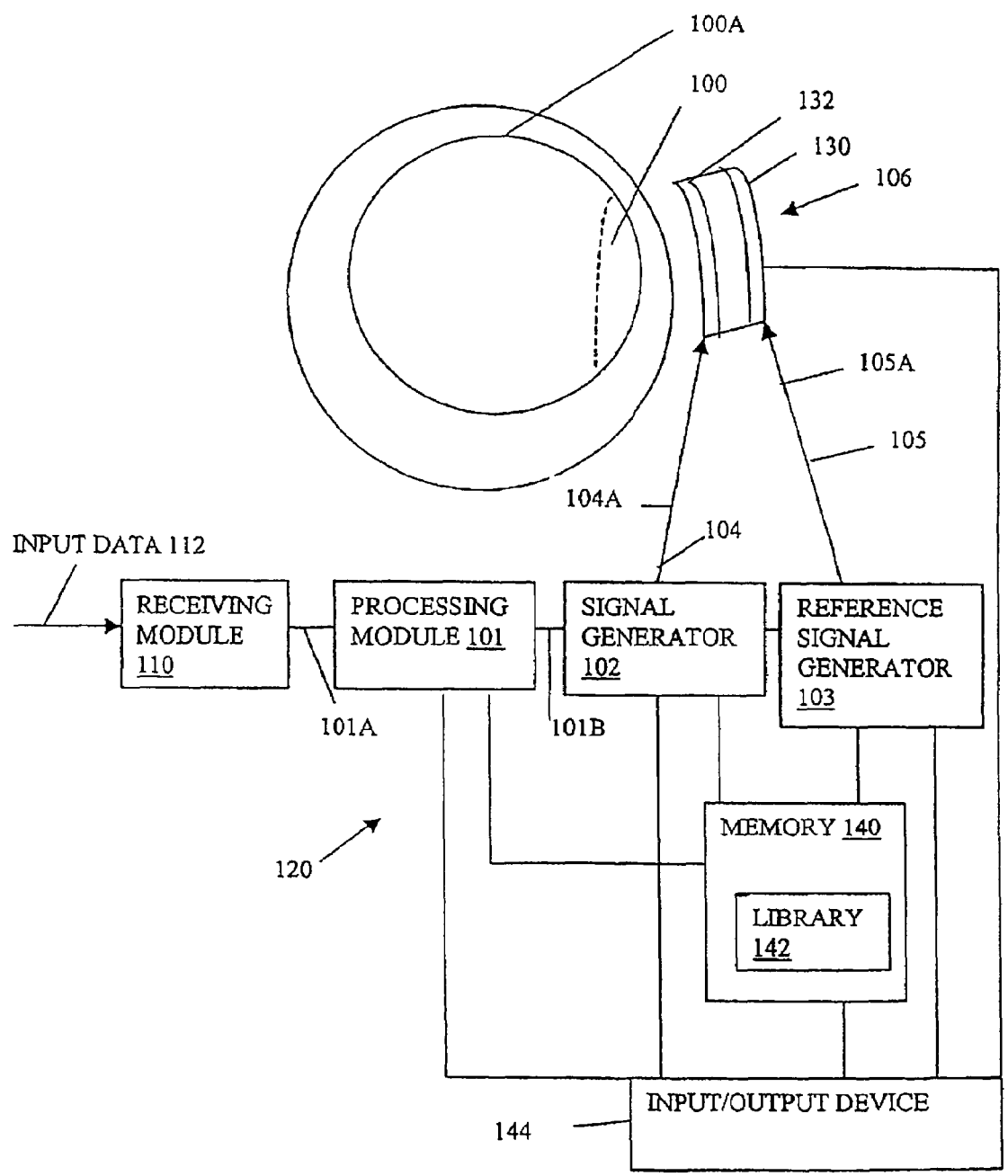
FIG. 1 illustrates one embodiment of a system for generating sensory data onto a human neural cortex.

FIG. 1 illustrates one embodiment of a system 120 in accordance with the present invention. FIG. 1 shows a visual portion 100 of the human cortex located in a person's brain 100A, such as for example, a vision-impaired person's brain. The system 120 of FIG. 1 is used with the visual cortex 100 merely as an example and is not intended to limit the scope of the invention. Instead of or in addition to the visual cortex 100, the system 120 may be used to stimulate neural activity in other areas of the nervous system. For example, the system 120 may be used as is or modified to generate audio, taste, smell and/or touch sensations within the brain 100A.

In FIG. 1, the system 120 comprises a receiving module 110, a processing module 101, a signal generator 102, a reference signal generator 103, a transducer system 106, a first signal line 104 and a second signal line 105. The receiving module 110, processing module 101, signal generator 102, and reference signal generator 103, may be referred to as, alone or in combination, a sensory data processing system. Various configurations of the system 120 may be configured in accordance with the present invention. The system 120 may comprise other modules and components in addition to or instead of the modules and components shown in FIG. 1.

In general, the system 120 receives, analyzes and transfers the sensory data 112 to the human brain 100A. The receiving module 110 receives sensory input data 112. Such data 112 may comprise live video data captured by a video camera (not shown), which a vision-impaired person may not be able to see. The sensory data 112 may be live or recorded.

The data 112 may be generated by other sources, such as for example a VCR, a DVD player, a cable broadcast, a satellite broadcast, an Internet connection, etc.

The processing module 101 receives input data 101A from the receiving module 110 and formats or converts the data 101A. For example, analog input data from the receiving module 110 may be digitized and/or converted into a neural firing time difference pattern. In one embodiment, the system 120 uses a technique that is reversed from a technique disclosed in "Reconstruction of Natural Scenes from Ensemble Responses in the Lateral Geniculate Nucleus" by Garrett B. Stanley et al. in the Sep. 15, 1999 issue of the Journal of Neuroscience, which is hereby incorporated by reference in its entirety.

Processed data 101B is transferred to the signal generator 102. Based upon the data 101B, the signal generator 102 generates a first signal 104A on the first line 104. The reference signal generator 103 generates a reference signal 105A on the second line 105. Both signals 104A and 105A are transferred to a transducer system 106.

The embodiment of a system 120 for generating sensory data onto a human neural cortex may also comprise a memory 140 and an input/output device 144.

One or more of the components illustrated in FIG. 1, such as the transducer system 106, may be specially configured to generate visual, audio, taste, smell and/or touch within the human neural cortex. In one embodiment, some or all of the components of FIG. 1 may be integrated in a lightweight, compact device that may be strapped to a user, e.g., in a backpack or belt pack.

In FIG. 1, the memory 140 is coupled to at least the signal generator 102 and/or the reference signal generator 103. The memory 140 may comprise any suitable type of memory that is preferably compact and adapted for fast memory access. The input/output device 144 is coupled to at least the memory 140. The input/output device 144 may comprise a keypad, a mouse, a display or other type of suitable input/output device that allows an administrator or user to calibrate the components of the system 120 and/or modify the data stored in the memory 140.

The memory 140 stores a library 142 of neural firing time data and/or neural firing time difference data. The system 120 uses the data in the library 142 to generate an acoustic signal or pattern, which alters, e.g., speeds up or slows down, one or more neural firing times of the human brain 100A. The patterns may affect various portions of the brain 100A substantially simultaneously. For example, the transducer system 106 may use signal phase shifts between two ultrasonic sources, such as the primary and secondary transducer arrays 130, 132, to produce specific pulse patterns that modify the firing times of targeted neurons. In one embodiment, the transducer system 106 produces a high frequency pattern that is pulsed at low frequencies. Altering the neural firing times causes a user to perceive sensory experiences.

The resolution, color, accuracy and other characteristics of the generated sensory experiences may vary according to the type of transducers used, the amount of neural firing time data stored in the library 142, and the processing power and speed of the system 120. For example, high resolution may be achieved with a large amount of neural firing time data and transducer arrays configured to focus acoustic signals to very small areas of the brain 100A.

The neural firing time data is obtained by reversing or inverting the acts of a technique described in "Reconstruction of Natural Scenes from Ensemble Responses in the Lateral Geniculate Nucleus" by Garrett B. Stanley et al. in the Sep. 15, 1999 issue of the Journal of Neuroscience, which is hereby incorporated by reference in its entirety. Garrett et al. describe a technique of reconstructing spatiotemporal natural scenes by linearly decoding ensemble responses within the lateral geniculate nucleus (177 cells) of a cat. The present method and system reverses Garret's technique in order to convert sensory data to neural firing time data and use a pattern of ultrasound signals based on the neural firing time data to alter neural firing times within the brain 100A. The altered neural firing times, i.e., neural firing time differences, generate sensory experiences for the user.

The use of single ultrasound pulses to modify nerve excitability is described in "Transient Modification of Nerve Excitability In Vitro by Single Ultrasound Pulses" by Mihran et al. found in the Department of Electrical and Computer Engineering, University of Colorado, 1990, paper #90-038, which is hereby incorporated by reference in its entirety. Human hearing and the action of ultrasound are described in "Human Hearing In Connection With The Action of Ultrasound In The Megahertz Range On The Aural Labyrinth" by L. R. Gavrilov in the Sov. Phys. Acoust. 26(4), July-August 1980 pages 290-292, which is hereby incorporated by reference in its entirety.

During manufacture of the system 120, a manufacturer may configure and store data in the memory 140, as well as calibrate the components of the system 120. The library 142 may comprise pre-determined or tested data related to different signals which are categorized into groups, such as signals generating visual experiences, signals generating auditory experiences, signals generating tactile experiences, etc. The groups may be further sub-categorized based on the size, shape, bright or dark, color, duration, pitch, etc. of the sensory experiences.

The library 142 may be complete, partially incomplete or substantially empty after manufacturing. An administrator at a user site may use the input/output device 144 to modify or add data in the library 142 based on responses from a current user or a previous user of the system 120.

In one embodiment, there is a library of various signals that may be applied to each neural location of the brain 100A or a part of the brain, such as the visual cortex 100. For example, if there are 100 neural locations mapped, then there may be 100 libraries of signals. As used herein, a neural location may comprise a single neuron or a group of neurons.

In one embodiment, there is a library of various signals for each transducer element in the primary and secondary transducer arrays 130, 132. The transducer arrays 130, 132 may be two-dimensional or three-dimensional arrays. A desired ultrasonic pattern in the brain 100A generated by the primary and secondary transducer arrays 130, 132 (e.g., phased arrays) may be calculated by adding the waves generated by each transducer element.

Figure 2:
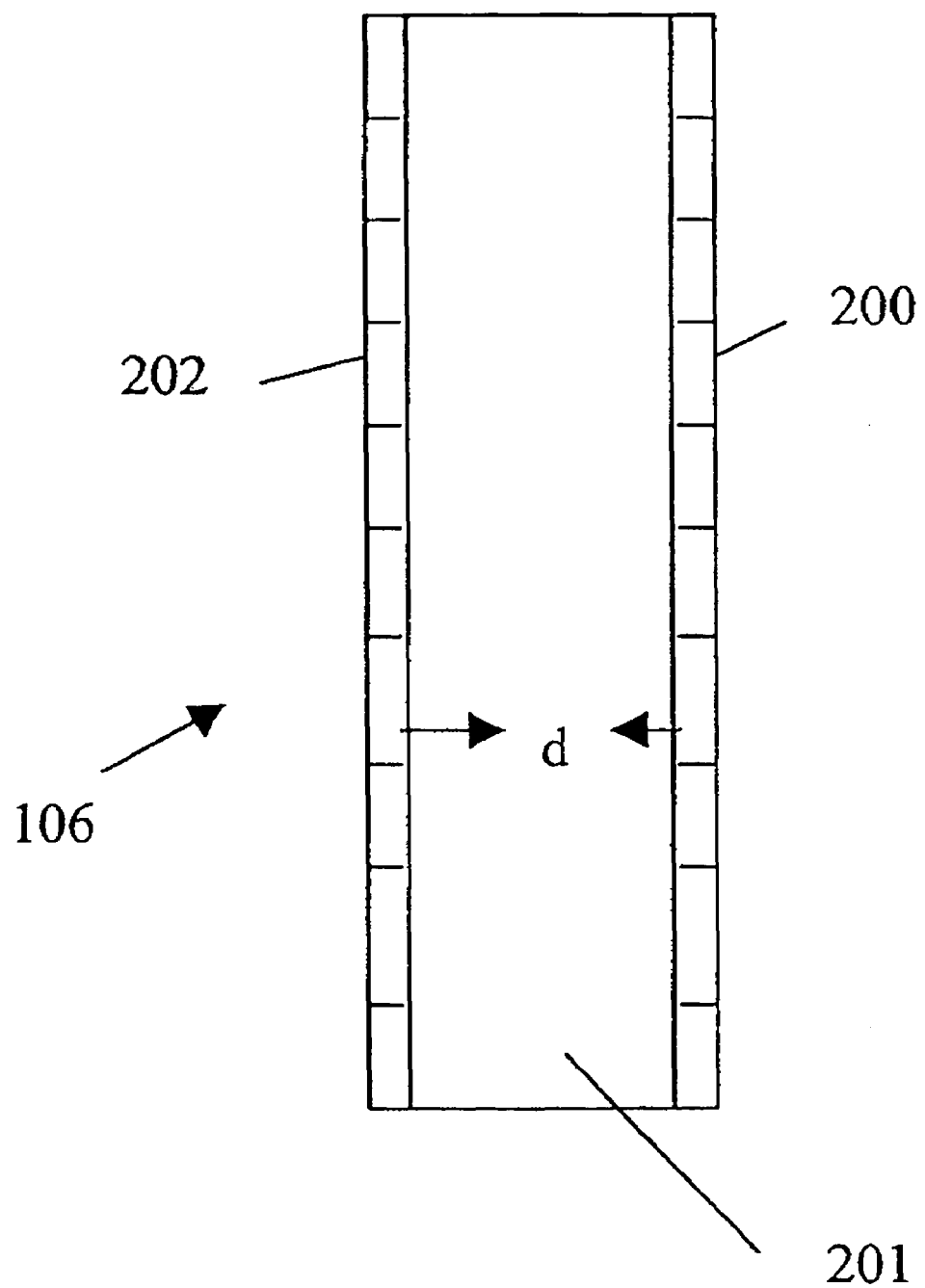
FIG. 2 illustrates one embodiment of a transducer system within the system of FIG. 1.

FIG. 2 illustrates one embodiment of a transducer system 106 within the system 120 of FIG. 1. The transducer system 106 includes a primary (or first) transducer array 200, and a secondary (or second) transducer array 202. An aperture 201 with a distance "d" separates the primary and secondary arrays 200 and 202. The distance 201 may be fixed or adjusted depending on the wavelength of energy emitted by primary array 200. In one embodiment, the distance 201 is equal to the wavelength of sound emitted by the primary transducer 200.

The primary transducer array 200 may comprise one or more columns and rows of individually controllable piezo-electric elements. The secondary transducer array 202 may also comprise a two-dimensional array of individually controllable piezoelectric elements.

In one embodiment, the primary and/or secondary transducer array 200, 202 each comprises a thin sheet of metal, glass, plastic or ceramic material covered with a two-dimensional array of individually controllable piezoelectric elements. Each element in the arrays 200, 202 may emit a unique signal. The arrays 200, 202 may or may not be flat and may be shaped to conform to a portion of the human head over which the transducer system 106 lays to provide better focusing. The layout of individual elements within each array 200, 202 can also be altered to provide better focusing, according to the shape of the area of the human cortex where signal 104A is to be projected.

In one embodiment, the arrays 200, 202 comprise piezoelectric elements that are held together by a flexible material, such as plastic or rubber. This embodiment allows the arrays 200, 202 to further conform to a portion of the human head over which the transducer system 106 lays to provide better focusing.

The primary and secondary transducer arrays 200 and 202 are arranged such that the primary array 200 acts as a source of coherent energy, while the secondary array 202 acts as a programmable diffraction grating. For example, the primary transducer array 200 may comprise a phased array of emitters, whereby the combined output of some or all of the emitters appears to the secondary transducer array 202 as a coherent acoustical signal source. The primary array 200 may emit acoustical energy, thereby providing an acoustical implementation of projective holography. In one embodiment, the phase of one or more array elements in the primary array 200 is controllable to allow shaping of the energy received by the secondary transducer array 202. The primary and secondary arrays 200 and 202 may emit ultrasonic energy at the same wavelength.

The secondary transducer array 202 may comprise an array of emitters, where each emitter can be individually controlled for amplitude and phase relative to the energy emitted by primary transducer 200. Changes in signal amplitude and phase are driven by signal 104A. The secondary array 202 may provide focusing and low frequency modulation of phase differences and/or signal amplitude between the energy emitted by the arrays 200, 202. The modulation of phase differences and/or signal amplitude induces low frequency vibrations in the neurons of the visual cortex 100. The focusing effect is accomplished by the primary array 200 acting as a coherent signal source, and the secondary array 202 acting as a controllable diffraction pattern, based upon signals 104A and 105A.

Ultrasonic frequencies may accurately place signal patterns within the cortex. Interaction of emissions from the primary and secondary arrays 200, 202 projects an interference pattern (e.g., low frequency signals or pulses) in the brain 100A. The projected interference pattern creates a highly defined pattern within the visual cortex 100 or another other part of the human neural cortex. Each point in the pattern may have an individually pulsed low frequency amplitude that is used to modify neural firing times.

Low frequency amplitude modulation combined with wavelength phase interactions from the primary and secondary transducer arrays 200, 202 form a stimulus to activate neurons in the visual cortex area 100 or another other part of the human neural cortex. By controlling the pattern of signal amplitude and phase shifts in secondary array 202, a wide range of patterns can be focused towards visual cortex 100 or any other region of the human cortex. Ultrasonic signals altering neural firings are discussed in "Temporally-specific modification of myelinated axon excitability in vitro following a single ultrasound pulse" by Mihran et al. published by the Ultrasound Med Biol 1990, 16(3), pp. 297-309 and "Transient Modification of Nerve Excitability In Vitro by Single Ultrasound Pulses" by Mihran et al. found in the Department of Electrical and Computer Engineering, University of Colorado, 1990, paper #90-038, which are hereby incorporated by reference in their entirety.

Changes in the neural firing timing induce various sensory experiences depending on the location of the firing timing change in the cortex. The mapping of sensory areas of the cortex is known and used in current surgically invasive techniques.

Figure 3:
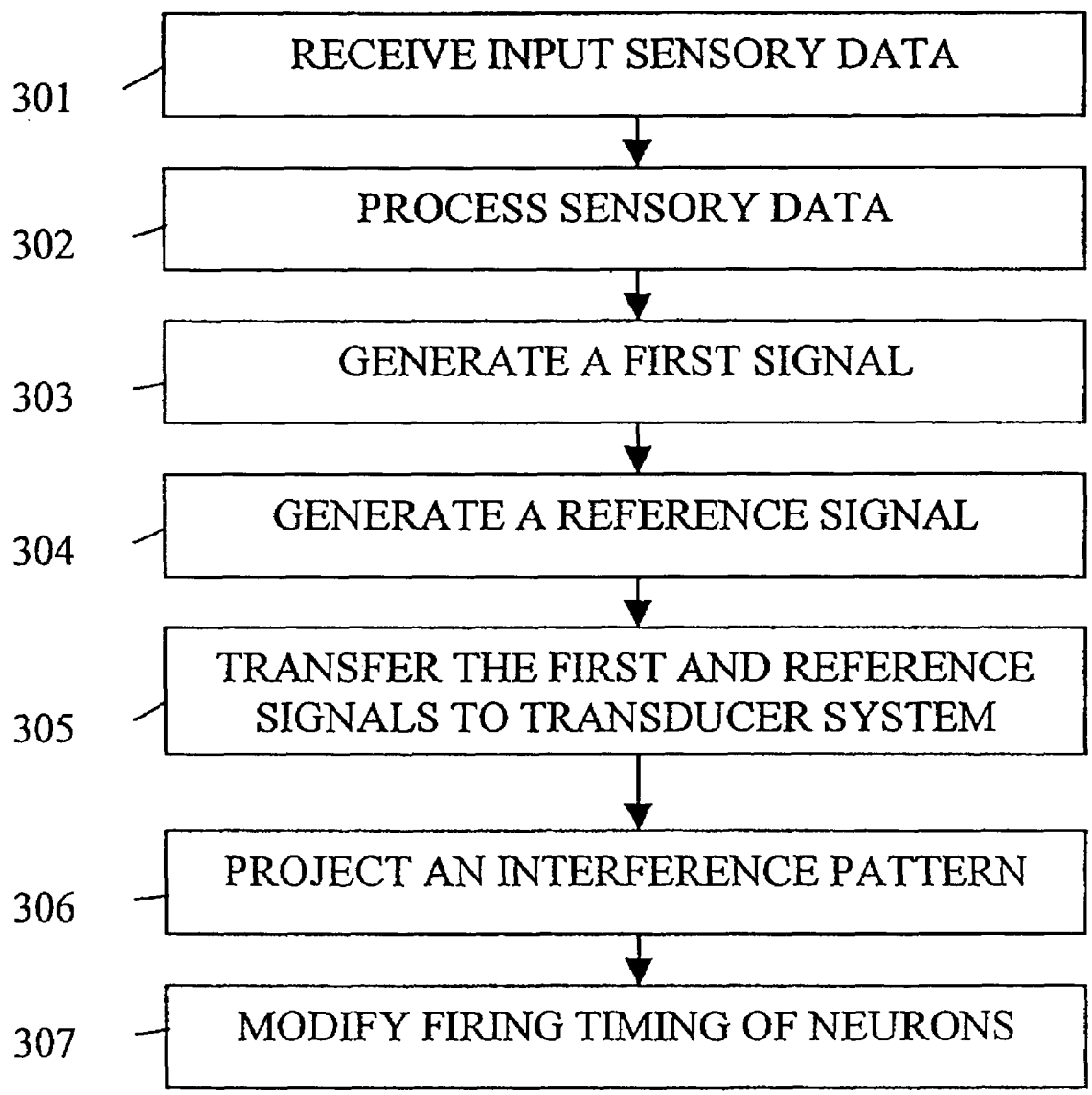
FIG. 3 illustrates one embodiment of a process in accordance with the present invention.

FIG. 3 illustrates one embodiment of a process in accordance with the present invention. In a process block 301, the receiving module 110 (FIG. 1) receives sensory input data 112 from, for example, a video camera, VCR, DVD player, cable broadcast, satellite broadcast, and/or Internet connection. The receiving module 110 outputs the data 101A to the processing module 101 (FIG. 1).

In a block 302, the processing module 101 processes the input data 101A. As stated above, in one embodiment, the processing module 101 digitizes analog data 101A from the receiving module 110 and/or converts the data 101A into a set of neural firing time differences or a pattern.

In a block 303, the signal generator 102 converts the firing time differences to a first signal 104A. For example, the first signal 104A may comprise an acoustical pattern, which comprises a plurality of amplitude and phase differences. In one embodiment, this conversion is accomplished by using known techniques in generating projective holograms. Acoustic holography is discussed in "Nearfield acoustic holography: I. Theory of generalized holography and the development of NAH" by J. D. Maynard et al. in the October 1985 issue of the Journal of the Acoustical Society of America, which is hereby incorporated by reference in its entirety.

In a block 304, the reference generator module 103 generates a reference signal 105A, which provides a coherent signal source, onto the second line 105. In one embodiment, the acts described in blocks 303 and 304 occur substantially simultaneously.

In a block 305, signals 104A and 105A are transferred to transducer system 106. The first signal 104A is transferred to the secondary array 202. The reference signal 105A is transferred to the primary array 200.

In a block 306, the transducer arrays 200 and 202 project a focused interference pattern onto the human cortex. The shape of the interference pattern and the amplitude pulse rate for each portion of the pattern may be controlled through the signals transferred in block 305. Low frequency pulses are derived from the interaction of the emissions from the primary and secondary arrays 200, 202.

In a block 307, low frequency pulsing of different points of the projected ultrasonic energy modifies the firing timing of the neurons in the human nervous system (in this example, the visual cortex 100), thereby giving rise to perceived sensory experiences, such as visual images. Sensory data is mapped in the neural cortex as differences in neural firing times. Thus, altering the firing times in cortical neurons can generate sensory experiences.

One advantage of the present system is that no surgery is needed to change neural activity causing a sensory experience.

Figure 4:
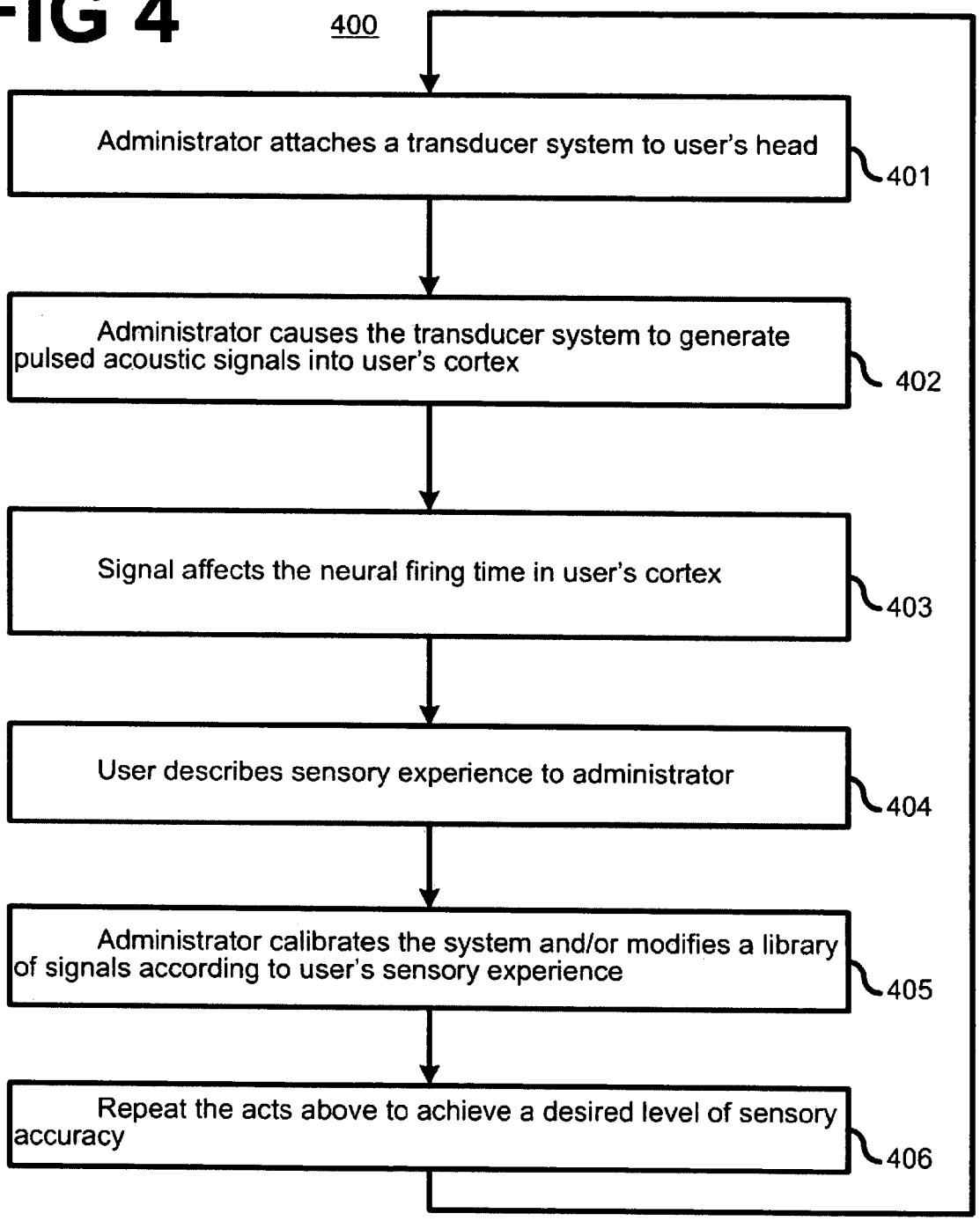
FIG. 4 illustrates a method for calibrating the system of FIG. 1, which generates sensory data onto a human neural cortex.

FIG. 4 illustrates an exemplary embodiment 400 of a method for calibrating or configuring the system 120 of FIG. 1, which generates sensory data onto a human neural cortex of a particular user's brain 100A. In a block 401, the administrator attaches the transducer system 106 in FIG. 1 non-invasively to a user's head and powers on the system 120. In one embodiment, the transducer system 106 is positioned near the back of the user's head to be closer to the visual cortex 100. The transducer system 106 may be attached and removed by the administrator or the user.

In block 402, the administrator causes the transducer system 106 to generate a high frequency acoustic signal(s)/pattern pulsed at low frequencies into the user's brain 100A shown in FIG. 1. An initial signal may be called a 'test signal.'

In a block 403, the signal(s) affects, e.g., speeds up or slows down, one or more neural firing times in the user's brain 100A, such as the visual cortex 100.

In a block 404, the user describes a sensory experience to the administrator. For example, if the transducer system 106 is configured to generate sensory experiences in the visual cortex, the user may experience a flashing light, a ramp from a bright area to a dark area, or an object at a particular location of the user's simulated visual field. If the transducer system 106 is configured to generate sensory experiences in the cochlear channel, the user may experience a sound of a particular frequency, amplitude and duration.

In a block 405, the administrator may calibrate the system 120 based on the user's described sensory experience. For example, the administrator may calibrate the processing module 101, the signal generator 102, the reference signal generator 103 and/or the transducer system 106 based on the user's described sensory experience. If the signal was supposed to generate a bright white square in the top left corner of the user's simulated visual field, the administrator may calibrate the system 120 such that the user will perceive a bright white square the next time a signal is sent. The administrator may use the input/output device 144 or some other suitable device to calibrate the system 120.

Instead of or in addition to calibrating the system 120, the administrator may modify the data in the library 142 stored in the memory 140 based on the user's described sensory experience. The administrator may also enter new data associated with the primary and/or secondary transducer arrays 130, 132 into the library 142 with the input/output device 144.

In a block 406, the administrator may repeat the acts in blocks 401-405 a plurality of times to fill a partially incomplete library 142 and/or to achieve a level of sensory accuracy or resolution desired by the administrator or the user. Subsequent signals may vary in frequency, amplitude, duration and location. For example, the administrator may use the system 120 to create a map of various signals with various characteristics applied to various locations of the brain 100A or a part of the brain 100A that correspond to various perceived visual images.

In one embodiment, the administrator uses the system 120 to create a 'visual field' of perceived visual 'pixels' in memory 140 by testing a plurality of neural locations in the visual cortex 100. The 'pixel' may vary from light to dark or from colored to non-colored. The administrator may use the system 120 to map several degrees of light or color intensity for each pixel. The resolution of the visual field depends on (i) the focusing capability of the transducer system 106, (ii) a number of different neural locations tested by the administrator, and (iii) a number of different neural firing time differences applied at each neural location by the administrator slightly altering the amplitude, frequency, etc. of the test signal. Thus, the system components and/or the library 142 may be customized to each individual user.

Data in a library 142 may be transferred from memory 140 to other memories or to a database. Various transfer methods may be used, including wire, cable, and wireless communication systems.

Figure 5:
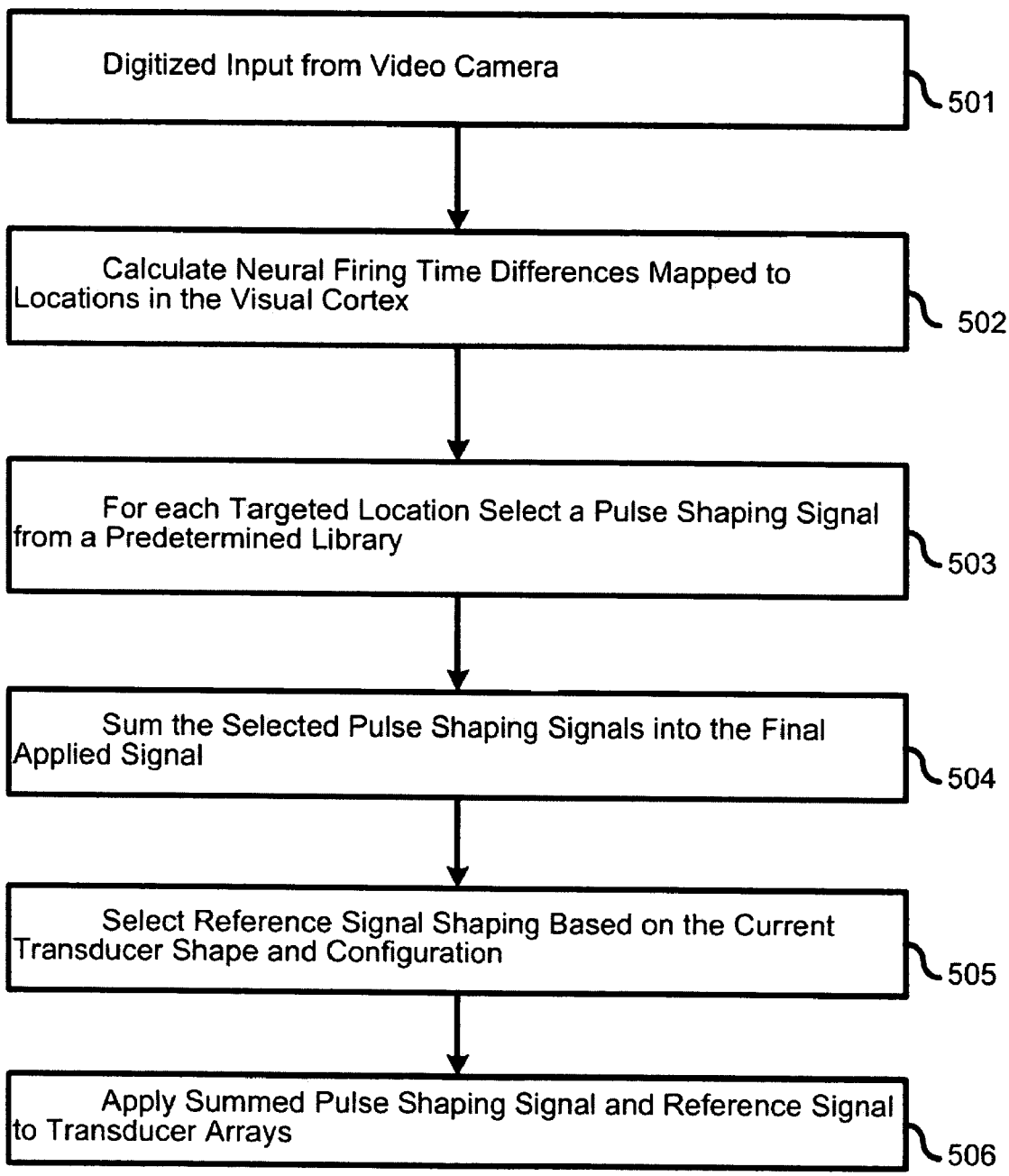
FIG. 5 illustrates a method of generating sensory data onto a human neural cortex with the system of FIG. 1.

FIG. 5 illustrates an exemplary embodiment 500 of a method of generating sensory data onto a human neural cortex. The system 120 may be configured to generate live or recorded images, videos, textual pieces, sounds, audio pieces, smells, taste and tactile sensations. In a block 501, the receiving module 110 of FIG. 1 receives a sensory input from a video camera or other source, such as a VCR, a DVD player, a cable TV system, an Internet connection, etc. The sensory input may be transmitted by a wire or wireless communication system. For example, for a vision-impaired user, the video camera may be strapped on or near the user's head such that the angle of the camera changes as the user turns his or her head. Alternatively, the video camera may be configured to move according to a hand-controlled device, such as a computer game joystick. The sensory input may comprise digital data or analog data. If the input data is analog, the processing module 101 may digitize the input data.

In a block 502, the processing module 101 and/or the signal generator 102 calculates neural firing time differences for mapped locations of the visual cortex 100 based on the sensory input.

In a block 503, the signal generator 102 selects data in the library 142 that will be used by the transducer system 106 to generate signals and achieve the desired neural firing time differences in the brain 100A. In one embodiment, the signal generator 102 selects data from the library 142 related to at least one pulse shaping signal, e.g., phase shift, for each targeted location in the visual cortex 100. For example, if there are 900 targeted locations in the visual cortex 100, then the signal generator 102 selects an individual pulse shaping signal from the library 142 for each of the 900 neural locations. The selected signals may vary in amplitude, phase, and/or duration.

In a block 504, the signal generator 102 sums the selected pulse shaping signals into a final applied signal or pattern for the secondary transducer array 132.

In a block 505, the reference signal generator 103 may select a reference signal shaping based on one or more factors, such as (1) the size, shape and configuration of the transducer system 106, and (2) the type of signals used by the secondary transducer array. The transducer system 106 may comprise a variety of transducer shapes, sizes, configurations, etc. Data related to various reference signals, including reference signals to generate a planar wave, may be stored in the library 142. The reference signals may be configured and stored by a manufacturer when the system 120 is manufactured and/or modified by an administrator at a user site.

The reference signals generated by the primary transducer array 130 may focus or shape the pattern generated by the secondary transducer array 132. The reference signals may vary in amplitude, phase, and/or duration from the signals selected by the signal generator 102.

In a block 506, the signal generator 102 applies a summed pulse-shaping signal to the secondary transducer array 132, and the reference signal generator 103 applies a reference signal to the primary transducer array 130. The transducer arrays 132, 130 generate a pulsed, ultrasound signal(s) or pattern comprised of phase shifts to the brain 100A, and the user experiences a sensory experience based on the sensory input from the video camera or other input source. The generated sensory experience may not be exact, but the generated sensory experience at least gives the user an idea of the sensory input. For example, depending on the implementation, a user using the system 120 may be able to only 'see' an outline of objects in front of the video camera.

In one embodiment, the ultrasound signals or pattern may be continuous, such that the user perceives a visual image in real-time as the video camera receives the image. In another embodiment, the ultrasound signals or pattern may be almost continuous, such that the user perceives a visual image in almost real-time, i.e., a string of snap shots, as the video camera receives the image.

Various types of memories, input/output devices, caches, controllers, registers and/or processing components may be used in accordance with the present invention. The scope of the present invention is not limited to a particular type of memory, input/output device, cache, controller, register and/or processing component. Various embodiments of the system 160 may comprise other components in addition to or instead of the components shown in FIGS. 1 and 2 without departing from the scope of the invention. For example, the system 160 may comprise a sensory input device, additional memories, caches, controllers, registers and/or processing components.

Additional Embodiments

The embodiments described above provide a method and apparatus to write sensory data directly to the human neural cortex. These embodiments apply an acoustic signal to generate neural timing differences that result in perceived sensory experiences. Implanted arrays of electrodes produce a visual field of "dots" because the electrode locations are fixed and thus the neural timing difference is only between the tip of the electrode and the affected neural tissue (see FIG. 6).

Figure 6:
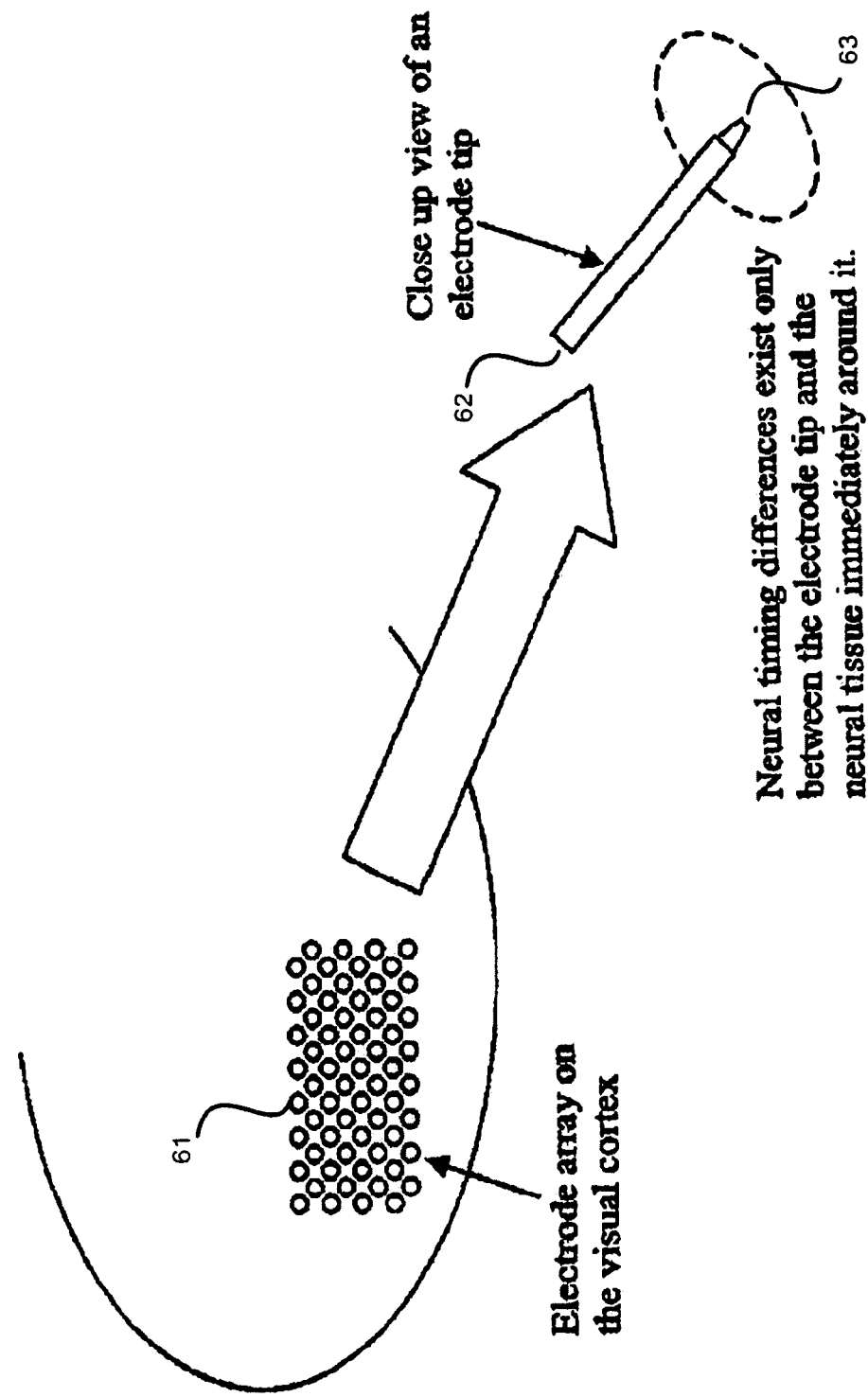
FIG. 6 illustrates an exemplary embodiment of an implantable electrode array for generating sensory data onto a human neural cortex according to one aspect of the present invention.

Turning to FIG. 6, shown there is an electrode array 61 that is disposed on the visual cortex. Element 62 is a detailed view of one of the electrodes in the array 61. Neural timing differences exist only between the electrode tip and the neural tissue immediately around it. The implanted electrode array 61 produces visual dot patterns. The fixed locations of the electrode tips 63 localize the neural timing differences to those pinpoint locations.

William H. Dobelle discusses dot pattern perception in Dobelle, William H., "Artificial Vision for the Blind by Connecting a Television Camera to the Visual Cortex" in the ASAIO Journal 2000. This article is hereby incorporated by reference as if repeated herein in its entirety.

Thus, a method is needed to stimulate an entire area of neural tissue rather than the selected pinpoint locations.

One aspect of the present invention comprises a method for scanning the neural cortex with an acoustic signal. As shown in FIG. 7, the acoustic signal is not applied as a static pattern but is dynamically scanned across the neural cortex at an array of locations. The dynamic feature of the signal allows an entire region of neural tissue to be stimulated. The pattern and scan directions used to simulate the neural tissue can be customized to the neural tissue that is to be affected.

Figure 9:
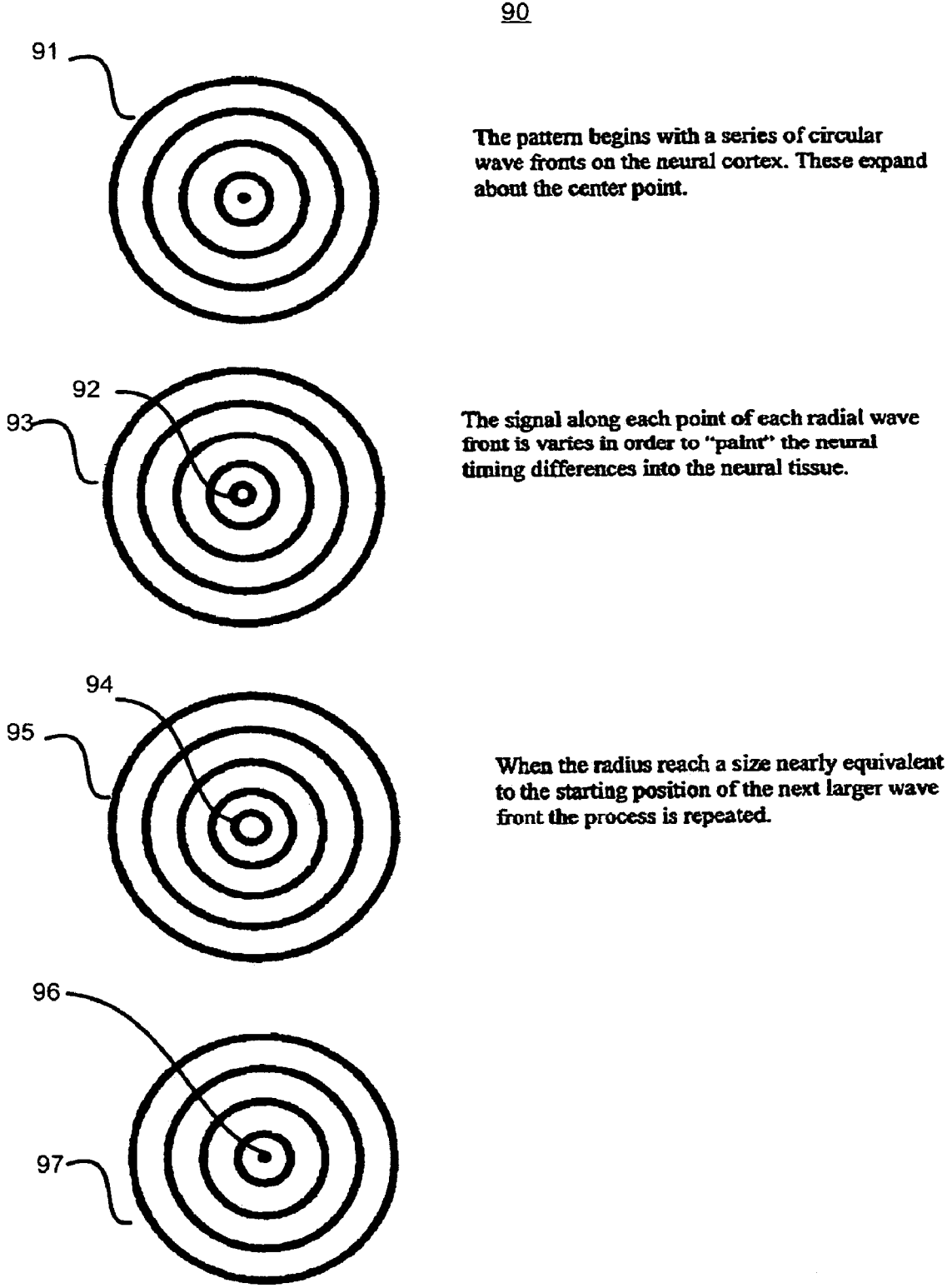
FIG. 9 depicts various patterns for shaping the acoustic signal used to activate the electrode array of FIG. 6 according to still another aspect of the present invention.

Some example variations in the scanning pattern are shown in FIGS. 8 and 9.

Unlike the fixed probes used in implanted techniques, in the acoustical techniques disclosed above, the acoustic energy moves across the video cortex allowing the acoustic energy to "paint" the timing difference information into the neural surface giving rise to perceived imagery. The embodiments herein allow a shaped acoustic wave front to be applied to the entire visual cortex. This dynamic wave front replaces the implanted arrays in the Dobelle article. The dynamic nature of the wave front creates neural timing differences over the entire surface allowing actual imagery to be perceived, whereas the static locations of the implanted electrodes in the referenced article are only capable of generating "dot" pictures.

As shown in FIG. 7, the acoustic signal 71, 72 sweeps across the visual cortex 73 generating differences in neural timing. Differences in neural timing result in perceived sensations, such as vision, hearing taste, etc. By replicating the neural timing differences that would have arisen from natural vision, artificial vision, as well as other sensory inputs, can be created. Thus, the acoustic signal 71 is initially directed at a first location in the visual cortex. The acoustic signal 72 then is directed at a second location in the visual cortex 73 at a later instant in time. Moreover, this process is repeated until the entire desired area of the visual cortex is scanned.

Turning to FIG. 8, shown therein is an exemplary embodiment 80 of a method for creating sensory experiences. As described above, the acoustic signal is scanned across the visual cortex to create the desired sensory perceptions. The acoustic signal is scanned in a predetermined pattern. In this exemplary embodiment 80, the pattern begins with an array of points on the visual cortex, as shown in the first block 81 of FIG. 8. Thus, an acoustic signal in an array of points is directed towards the visual cortex.

As shown in block 82, the acoustic pattern is then shaped to expand in radius about each point. Thus, the acoustic signal scans the visual cortex in an array of expanding circles. The outer edge of the circle represents the area of the visual cortex being scanned by the acoustic signal.

Only the tissue along the edge of each radius is affected at any moment. Varying the signal at each point along the radius as it expands produces neural firing differences in the neural tissue, as shown in the third block 83 of FIG. 8.

When the circles expand to where they begin to touch, the pattern changes to fill in the areas between the original point array, as shown in the fourth block 84 of FIG. 8.

The new circles 89 are centered about the points 88 between the original stimulation locations, and the acoustic signal contracts about these new centers 89, as shown in the fifth block 85 of FIG. 8.

The signal continues to contract about the new center points 89 as shown in the sixth block 86 of FIG. 8.

When the new circles have contracted to an array of points, the process can be repeated from the start or simply reversed.

Turning to FIG. 9, shown therein is another exemplary embodiment 90 of a method for shaping the acoustic signal to generate perceived sensory experiences in the human neural cortex. In this embodiment 90, the acoustic signal is a directed radial pattern that sweeps the cortical area with the signal pattern.

The pattern 91 begins with a series of circular wave fronts on the neural cortex. These wave fronts then expand about the center point 92, as shown in the first pattern 91 of FIG. 9. Thus, each concentric circle in the pattern expands from its initial size until reaching a size of its closest neighbor was initially.

The signal along each point of each radial wave front is varied to "paint" the neural timing differences into the neural tissue, as shown in the second pattern 93 of FIG. 9.

When the circles 94 reach a size nearly equivalent to the starting position of the next larger wave front, the process is repeated, as shown in the third pattern 95 of FIG. 9.

The pattern then ends as shown in the fourth pattern 97 of FIG. 9 and the process is repeated, as necessary.

Turning to FIG. 10, shown therein is an exemplary embodiment 1000 of a method for generating perceived sensory experiences using the above-mentioned acoustical signal techniques.

In element 1001, the acoustical signal is directed towards a predetermined location in the human neural cortex as a predetermined pattern.

In element 1002, the acoustical signal is scanned across the predetermined location in the human neural cortex by modifying the predetermined pattern so that the acoustical signal is applied to an entire region in the human neural cortex over a predetermined time period. In this embodiment 1000, the acoustical signal may comprise a pulsed ultrasonic signal formed from externally supplied neural timing difference data. The pulsed ultrasonic signal is then directed to the human neural cortex to modify a firing rate of neural tissue therein.

The above acts of directing and scanning can be repeated as desired to obtain the desired sensory experience.

Turning to FIG. 11, shown therein is an exemplary embodiment 1100 of a method for generating sensory experiences.

In element 1101, an acoustical signal is directed to a human neural cortex to form a first array of points on the visual cortex tissue.

In element 1102, the acoustical signal is modified to expand each of the points in the first array in a circle about each point until each of the circles touches one or more neighboring circles in the visual cortex tissue.

In element 1103, the acoustical signal is adjusted to move a center of each of the circles in the first array to one or more locations in unaffected tissue in the visual cortex to form a second array of circles.

In element 1104, the acoustical signal is modified to contract each of the circles in the second array about a new center point until reaching a dot at the new center point.

In element 1105, the acts above are repeated to achieve a desired level of sensory accuracy.

Turning to FIG. 12, shown therein is another exemplary embodiment 1200 of a method for generating sensory experiences.

In element 1201, an acoustical signal is directed to a human neural cortex to form a first array of a concentric circles on the visual cortex tissue.

In element 1202, the acoustical signal is modified to expand each of the circles in the first array of concentric circles about its center until each of the circles achieves a size approximately that of an original neighbor concentric circles in the visual cortex tissue.

In element 1203, the acts above are repeated to achieve a desired level of sensory accuracy.

The above-described embodiments of the present invention are merely meant to be illustrative and not limiting. It will thus be obvious to those skilled in the art that various changes and modifications may be made without departing from this invention in its broader aspects. The appended claims encompass all such changes and modifications as fall within the true spirit and scope of this invention. Although various embodiments are specifically illustrated and described herein, it will be appreciated that modifications and variations of the invention are covered by the above teachings and are within the purview of the appended claims without departing from the spirit and intended scope of the invention. For example, certain signals are described herein to create the desired results, however, other similar signals may be employed without departing from the scope of the present invention. Furthermore, this example should not be interpreted to limit the modifications and variations of the invention covered by the claims but is merely illustrative of one possible variation.

What is claimed is:

1. A method for generating perceived sensory experiences comprising:
   directing an acoustical signal toward a human neural cortex; and
   remedying a sensory deficit in a human patient by scanning the acoustical signal across the human neural cortex,
   wherein the acoustical signal is directed as an array of points, and
   wherein the acoustical signal is scanned across the human neural cortex by expanding each of the points in the array of points in a circle about each point until touching a neighboring circle in the array of expanding circles.

2. The method according to claim 1, wherein the acoustical signal comprises a pulsed ultrasonic signal formed from externally supplied neural timing difference data.

3. The method according to claim 2, wherein said directing further comprises directing the pulsed ultrasonic signal to the human neural cortex to modify a firing rate of neural tissue therein.

4. The method according to claim 1, wherein the array of expanding circles is shifted to be entered in spaces between the array of expanding circles.

5. The method according to claim 4, wherein each of the circles in the shifted array of circles is then contracted until reaching a center point.

6. The method according to claim 1, wherein the acoustical signal is directed as a predetermined pattern.

7. The method according to claim 6, wherein the acoustical signal is scanned across the human visual cortex by modifying the predetermined pattern to cover an entire region of the human visual cortex over a predetermined time period.

8. The method according to claim 1, wherein the acoustical signal is directed towards the human visual cortex as a pattern of concentric circles.

9. A method for generating perceived sensory experiences comprising:
   remedying a sensory deficit in the human patient by directing an acoustical signal to a human neural cortex to form a first array of a points on the visual cortex tissue; and
   modifying the acoustical signal to expand each of the points in the first array in a circle about each point until each of the circles touches one or more neighboring circles in the visual cortex tissue.

10. The method according to claim 9, further comprising:
    adjusting the acoustical signal to move a center of each of the circles in the first array to one or more locations in unaffected tissue in the visual cortex to form a second array of circles.

11. The method according to claim 10, further comprising: modifying the acoustical signal to contract each of the circles in the second array about a new center point until reaching a dot at the new center point.

12. The method according to claim 9, wherein the acoustical signal comprises a pulsed ultrasonic signal formed from externally supplied neural timing difference data.

13. The method according to claim 12, wherein said directing further comprises directing the pulsed ultrasonic signal to the human neural cortex to modify a firing rate of neural tissue therein.

14. A method for generating perceived sensory experiences comprising:
   remedying a sensory deficit in the human patient by directing an acoustical signal to a human neural cortex to form a first array of a concentric circles on the visual cortex tissue;
   modifying the acoustical signal to expand each of the circles in the first array of concentric circles about its center until each of the circles achieves a size approximately that of an original neighbor concentric circle in the visual cortex tissue.

15. The method according to claim 14, further comprising:
   repeating or reversing the modifying and directing steps.

16. The method according to claim 14, wherein the acoustical signal comprises a pulsed ultrasonic signal formed from externally supplied neural timing difference data.

17. The method according to claim 16, wherein said directing further comprises directing the pulsed ultrasonic signal to the human neural cortex to modify a firing rate of neural tissue therein.

* * * * *

UNITED STATES PATENT AND TRADEMARK OFFICE
CERTIFICATE OF CORRECTION

| | |
|---|---|
| PATENT NO. | : 7,350,522 B2 |
| APPLICATION NO. | : 10/823090 |
| DATED | : April 1, 2008 |
| INVENTOR(S) | : Thomas Patrick Dawson |

It is certified that error appears in the above-identified patent and that said Letters Patent is hereby corrected as shown below:

Col. 14, Claim 9, Line 50, after "of", delete -- a --.

Col. 15, Claim 14, Line 9, after "of", delete -- a --.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,350,522 B2
APPLICATION NO. : 10/823090
DATED : April 1, 2008
INVENTOR(S) : Thomas Patrick Dawson It is certified that error appears in the above-identified patent and that said Letters Patent is hereby corrected as shown below:

Specification, Col. 3, Line 21, after "signal", change "form" to -- from --.

Specification, Col. 3, Line 40, before "transducer", change "brain, the," to -- brain. The --.

Specification, Col. 7, Line 57, after "modulation", insert -- , --.

Specification, Col. 7, Line 59, after "202", insert -- , --.

Specification, Col. 7, Line 60, after "100", insert -- , --.

Specification, Col. 7, Line 60, after "another", delete "other".

Specification, Col. 12, Line 9, after "hearing", insert -- , --.

Specification, Col. 12, Line 58, after "reaching", change "a size of its closest neighbor was initially." to -- the initial size of its closest neighbor. --.

Specification, Col. 13, Line 44, before "concentric", delete -- a --.

Col. 14, Claim 9, Line 50, after "of", delete -- a --.

Col. 15, Claim 14, Line 9, after "of", delete -- a --.

Signed and Sealed this

Seventeenth Day of February, 2009

JOHN DOLL
*Acting Director of the United States Patent and Trademark Office*